(12) United States Patent
Hasegawa

(10) Patent No.: US 12,168,068 B2
(45) Date of Patent: Dec. 17, 2024

(54) HYDROPHILIZED ORGANIC POWDER AND COSMETIC INCLUDING HYDROPHILIZED ORGANIC POWDER

(71) Applicant: MIYOSHI KASEI, INC., Tokyo (JP)

(72) Inventor: Yukio Hasegawa, Tokyo (JP)

(73) Assignee: MIYOSHI KASEI, INC., Tokyo (JP)

( * ) Notice: Subject to any disclaimer, the term of this patent is extended or adjusted under 35 U.S.C. 154(b) by 531 days.

(21) Appl. No.: 17/629,584

(22) PCT Filed: Jul. 25, 2019

(86) PCT No.: PCT/JP2019/029293
§ 371 (c)(1),
(2) Date: Jan. 24, 2022

(87) PCT Pub. No.: WO2021/014654
PCT Pub. Date: Jan. 28, 2021

(65) Prior Publication Data
US 2022/0273549 A1   Sep. 1, 2022

(51) Int. Cl.
*A61K 8/42*  (2006.01)
*A61K 8/85*  (2006.01)
(Continued)

(52) U.S. Cl.
CPC .................. *A61K 8/86* (2013.01); *A61K 8/42* (2013.01); *A61K 8/85* (2013.01); *A61K 8/87* (2013.01); *A61K 8/89* (2013.01); *A61Q 17/04* (2013.01)

(58) Field of Classification Search
None
See application file for complete search history.

(56) References Cited

U.S. PATENT DOCUMENTS 8,105,691 B2   1/2012   Takeuchi et al.
9,434,819 B2   9/2016   Inokuchi et al.
(Continued)

FOREIGN PATENT DOCUMENTS

CN   103768151 A   5/2014
EP   1914264 A1   4/2008
(Continued)

OTHER PUBLICATIONS

Notification of Transmittal of Translation of the International Preliminary Report on Patentability (Form PCT/IB/338) issued in counterpart International Application No. PCT/JP2019/029293 mailed Feb. 3, 2022 with Forms PCT/IB/373 and PCT/ISA/237. (9 pages).
(Continued)

*Primary Examiner* — Brian Gulledge
(74) *Attorney, Agent, or Firm* — WHDA, LLP

(57) ABSTRACT

Provided are: a hydrophilized organic powder that is obtained by a hydrophilization treatment of a hydrophobic organic powder and has favorable properties; and a cosmetic that includes the hydrophilized organic powder. A hydrophilized organic powder that has a hydrophilizing-coat of polyoxyethylene (10) isostearyl ether on a hydrophobic organic powder is provided. Further, a cosmetic that includes the hydrophilized organic powder is provided. The hydrophobic organic powder is preferably an organic resin powder or a metallic soap powder, or a combination thereof.

4 Claims, 3 Drawing Sheets

(51) Int. Cl.
  *A61K 8/86*  (2006.01)
  *A61K 8/87*  (2006.01)
  *A61K 8/89*  (2006.01)
  *A61Q 17/04*  (2006.01)

(56) References Cited

U.S. PATENT DOCUMENTS

| | | | |
|---|---|---|---|
| 2005/0169867 A1 | 8/2005 | Horino et al. | |
| 2009/0263660 A1* | 10/2009 | Takeuchi | C08J 3/126 |
| | | | 428/407 |
| 2012/0010169 A1 | 1/2012 | Teshigawara et al. | |
| 2015/0118320 A1 | 4/2015 | Inokuchi et al. | |
| 2015/0329678 A1 | 11/2015 | Inokuchi et al. | |

FOREIGN PATENT DOCUMENTS

| | | |
|---|---|---|
| JP | 2005-213362 A | 8/2005 |
| JP | 2005-324981 A | 11/2005 |
| JP | 2013-112680 A | 6/2013 |
| JP | 2013-256450 A | 12/2013 |
| JP | 2015-086150 A | 5/2015 |
| JP | 2015-131782 A | 7/2015 |
| JP | 2015-143206 A | 8/2015 |
| JP | 2019-064935 A | 4/2019 |
| JP | 2019-094273 A | 6/2019 |
| WO | 2007/007521 A1 | 1/2007 |
| WO | 2010/110047 A1 | 9/2010 |
| WO | 2014/106768 A1 | 7/2014 |

OTHER PUBLICATIONS

Office Action dated Oct. 17, 2023, issued in counterpart CN Application No. 201980098761.6. (9 pages).

International Search Report dated Oct. 8, 2019, issued in counterpart International Application No. PCT/JP2019/029293. (2 pages).

Extended (Supplementary)European Search Report dated Apr. 11, 2023, issued in counterpart EP Application No. 19938703.6. (6 pages).

Notice of Allowance dated May 9, 2023, issued in counterpart to JP Application No. 2021-534521, with English Translation. (6 pages).

* cited by examiner

HYDROPHILIZED ORGANIC POWDER AND COSMETIC INCLUDING HYDROPHILIZED ORGANIC POWDER

FIELD

The present invention relates to a hydrophilized organic powder, and a cosmetic including a hydrophilized organic powder.

BACKGROUND

In recent years, a technology in which a hydrophobic powder is subjected to a hydrophilization treatment and blended in an aqueous layer of a cosmetic has been developed. For example, Patent Document 1 discloses a technology for hydrophilizing the surfaces of silicone particles by a plasma treatment. Further, a technology for performing a hydrophilization treatment of a hydrophobic powder using a nonionic surfactant has also been developed.

[Patent Literature 1] WO2014/106768A

SUMMARY

The following analysis was made from an aspect of the present invention. The disclosure of the above prior art document shall be incorporated into this document by reference.

There is a problem that desired properties cannot always be achieved when the hydrophobic powder is subjected to a hydrophilization treatment. For example, the hydrophilized silicone particles of Patent Document 1 have a problem that when the particles are left in the air, the hydrophilicity is lost with the passage of time and the particles return to the original hydrophobic particles. In addition, even if nonionic surfactants have similar configurations, some can achieve the desired property and some cannot, and it is necessary to select the nonionic surfactant in consideration of the desired properties. However, there is no knowledge that can guide the selection.

In view of this, an object of the present invention is to contribute to the provision of a hydrophilized organic powder including a hydrophobic organic powder as a base material and having hydrophilicity and other favorable properties, and a cosmetic including the hydrophilized organic powder.

According to a first aspect of the present invention, a hydrophilized organic powder having a hydrophilizing-coat of polyoxyethylene (10) isostearyl ether on a hydrophobic organic powder is provided.

In the first aspect described above, it is preferred that the hydrophobic organic powder is an organic resin powder, a metallic soap powder, or a combination thereof.

According to a second aspect of the present invention, a cosmetic comprising the hydrophilized organic powder of the first aspect is provided.

According to each aspect of the present invention, a technology that contributes to the provision of a hydrophilized organic powder comprising a hydrophobic organic powder as a base material and having hydrophilicity and other favorable properties, and a cosmetic comprising the hydrophilized organic powder is provided.

MODES

Figure 1:
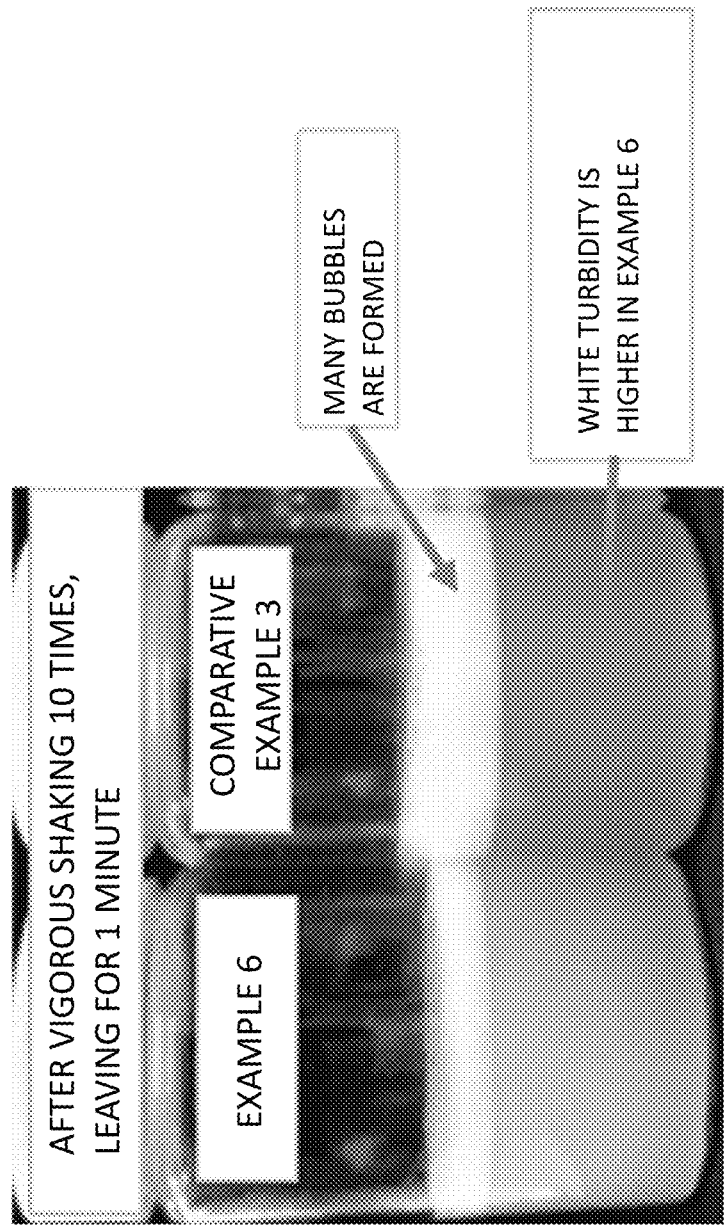
FIG. 1 shows an example of an evaluation result of the hydrophilicity of a hydrophilized organic powder of the present invention.

First, terms used in the present application will be explained.

[Polyoxyethylene (10) Isostearyl Ether]

Polyoxyethylene (10) isostearyl ether means a nonionic surfactant in which polyoxyethylene (10) and isostearyl alcohol are bonded through an ether bond. Polyoxyethylene (10) means a portion (moiety) in which 10 molecules of ethylene oxide are polymerized. The type of isostearyl alcohol includes a Guerbet type, a methyl branched type, and a multi-branched type, but it may be of any type. Here, the degree of polymerization of ethylene oxide is generally an average value or a peak value of the number of added molecules of ethylene oxide, and for example, in polyoxyethylene (10), polyoxyethylene (9), polyoxyethylene (11), or the like can be presented in a mixed state. In general, the degree of polymerization of ethylene oxide is also represented by the number of moles added.

Examples of generally available polyoxyethylene (10) isostearyl ether include Nonion IS-210 of NOF Corporation and EMALEX 1810 of Nihon Emulsion Co., Ltd. The HLB of polyoxyethylene (10) isostearyl ether is 12.4. Here, the HLB can be obtained from, for example, the formula defined by the Griffin method shown below.

$$HLB = (\text{Molecular weight of hydrophilic portion in surfactant}/\text{Molecular weight of surfactant}) \times 20$$

[Hydrophobic Organic Powder]

The hydrophobic organic powder means an organic powder that exhibits hydrophobicity by itself, and particularly means a powder used as a base material of a hydrophilized organic powder in the present application. Here, hydrophobicity by itself means, for example, a property in which when 100 cc of ion exchanged water is placed in a 200 cc glass beaker and 1.0 g of an organic powder is added thereto and the mixture is left to stand for 1 hour, all or most of the particles of the organic powder do not transfer to the aqueous layer.

Concrete examples of the hydrophobic organic powder include an alkyl (meth)acrylate powder, a polyethylene powder, a polypropylene powder, a polystyrene powder, a polyethylene terephthalate powder, a polytetrafluoroethylene powder, a polyurethane powder, a polylactic acid powder, and a nylon 12 powder, powders of organic resins such as octanoyl lysine, lauroyl lysine, and acylated lysine, organic resin powders such as a silicone elastomer powder, and silicone powders of polymethylsilsesquioxane and the like, and metallic soap powders of calcium stearate, zinc stearate, magnesium stearate, and the like.

The average particle diameter of the hydrophobic organic powder is desirably in the range of 0.1 to 500 μm. The particle shape may be any shape such as a spherical, hemispherical, flaky, acicular, or amorphous shape. A hydrophobic powder obtained by treating a hydrophilic inorganic powder (for example, a metal oxide or a metal hydroxide) with an organic hydrophobization treatment agent itself (the base material of the powder) cannot be said to be hydrophobic in the first place, and is also merely configured such that the inorganic powder is coated with the organic hydrophobization treatment agent, and therefore, it is not referred to as a hydrophobic organic powder in the present application.

Examples of the hydrophobic organic powder generally available as a silicone powder include KSP-100, KSP-101, KSP-102, KSP-105, KSP-300, KSP-411, KSP-441, KMP-590, and KMP-591 of Shin-Etsu Chemical Co., Ltd. Further, examples of the hydrophobic organic powder generally available as a polyethylene terephthalate powder include Snow Leaf P and Snow Leaf PF. Examples of the polyurethane powder include DAIMIC BEAZ manufactured by Dainichiseika Co., Ltd., examples of the metallic soap powder include Calcium Stearate S, Aulabrite NC, Aulabrite NM, and Zinc Stearate S of NOF Corporation, and examples of the amino acid powder include Amihope LL that is lauroyl lysine and Amihope OL that is caproyl lysine.

[Hydrophilized Organic Powder]

In the present application, the hydrophilized organic powder means a powder having a hydrophilizing-coat formed by a hydrophilization treatment of a hydrophobic organic powder. In the present application, concretely, a powder including a hydrophobic organic powder as a base material and having a hydrophilizing-coat of polyoxyethylene (10) isostearyl ether is provided.

The hydrophilization treatment method is not particularly limited, and the preparation can be carried out by mixing and drying polyoxyethylene (10) isostearyl ether and the organic powder while being in contact with each other. The mixing method is also not particularly limited, and a mixing machine capable of uniformly performing the treatment may be adopted. For example, a Henschel mixer, a ribbon blender, a kneader, an extruder, a disper mixer, a homomixer, a wet jet mill, a bead mill, and the like are exemplified. When the solvent is removed after mixing, drying is performed with a hot air dryer, a spray dryer, a flash dryer, a conical dryer, or the like, and if necessary, processing is performed using a crusher such as a pin mill, an atomizer, or a dry jet mill, whereby the hydrophilized organic powder can be obtained.

The blending ratio of polyoxyethylene (10) isostearyl ether (A) and the hydrophobic organic powder (B) is (A)/(B)=0.05/99.95 to 10.0/90.0 (wt %). The blending ratio is preferably 0.1/99.9 to 7.0/93.0 (wt %), and more preferably 0.1/99.9 to 5.0/95.0 (wt %). The intermediate numerical range or any intermediate value is also possible without being specified and is considered to be described. The blending amount of the surfactant (that is, polyoxyethylene (10) isostearyl ether) is preferably as small as possible from the viewpoint of irritation to the skin.

[Aqueous Dispersion]

An aqueous dispersion means a liquid in which the hydrophilized organic powder is dispersed in a water-based (or aqueous) solvent containing water as a main component. For example, by preparing an aqueous dispersion as a material of a cosmetic, an advantage that the hydrophilized organic powder can be prevented from scattering when producing the cosmetic, or the like is obtained.

When an aqueous dispersion is prepared as a material of a cosmetic, other components that are compatible with water can also be blended.

Examples of such other components include alcohols such as ethanol, a polyhydric alcohol, propylene glycol, dipropylene glycol, 1,3-butylene glycol, polyethylene glycol, glycerin, diglycerin, polyglycerin, hexylglycerin, cyclohexylglycerin, trimethylolpropane, xylitol, erythritol, trehalose, and sorbitol. The blending ratio of water and an alcohol is water/alcohol=100/0 to 50/50 (wt %), but the blending ratio of the alcohol is preferably as low as possible.

In addition, as the other components of the aqueous dispersion, a surfactant, a moisturizer, an organic UV absorber, a preservative, an antioxidant, a coat forming agent, a thickener, a dye, a pigment, various chemicals, a fragrance, or the like can be appropriately blended.

As the surfactant, a nonionic surfactant, particularly, polyoxyethylene (10) isostearyl ether is used, but when the surfactant is blended as a composition of a cosmetic, the sense of use is slightly deteriorated as shown in the following Examples 9 and 10, and therefore, it is clearly distinguished from one used at the time of preparing the hydrophilized organic powder (one for the use of the present invention).

Examples of the thickener include sodium hyaluronate, cationized sodium hyaluronate, a polymer and a copolymer having acryloyldimethyltaurine or a salt thereof as a constituent unit, and polyvinylpyrrolidone. Concrete examples thereof include (sodium acrylate/acryloyldimethyltaurate/dimethylacrylamide) crosspolymer (trade name: SEPINOV P88; Seiwa Kasei Co., Ltd.), polyacrylate crosspolymer-6 (trade name: SEPIMAX ZEN; Seiwa Kasei Co., Ltd.), (hydroxyethyl acrylate/sodium acryloyldimethyltaurate) copolymer (trade name: SEPINOV EMT 10; Seiwa Kasei Co., Ltd.), polyvinylpyrrolidone (trade name: Luviskol K17, Luviskol K30, Luviskol K90; BASF Japan Ltd.), a (PEG-240/decyltetradeceth-20/HDI) copolymer/potassium laurate/BG/water mixture (ADEKA NOL GT-730; ADEKA Corporation), a polyurethane-59/BG/water mixture (ADEKA NOL GT-930; ADEKA Corporation), Trideses-6 (Avalure Flex-6 CC Polymer; Lubrizol Corporation), Xanthan gum (KELTROL CG-T; Sansho Co., Ltd.), gellan gum (Kelcogel, Kelcogel HM; DSP Gokyo Food & Chemical Co. Ltd.), silicic acid (Na/Mg) (trade name: OVEIL ER (Osaka Gas Chemical Co., Ltd.)) and bentonite (trade name: OVEIL BR (Osaka Gas Chemical Co., Ltd.)).

[Cosmetic]

The cosmetic includes a makeup cosmetic, a skin care cosmetic, a hair cosmetic, and the like. Examples of the makeup cosmetic include a makeup base, a white powder foundation (water-based, oil-based), a powder foundation, a liquid foundation, a W/O-type emulsion foundation, an oily foundation, an oily solid foundation, a stick foundation, a pressed powder, a face powder, a white powder, a lipstick, a lipstick overcoat, a lip gloss, a concealer, a cheek color, an eye shadow (water-based, oil-based), an eyebrow, an eyeliner, a mascara, an aqueous nail enamel, an oily nail enamel, an emulsion nail enamel, an enamel top coat, and an enamel base coat. Examples of the skin care cosmetic include an emollient cream, a cold cream, a whitening cream, a milky lotion, a toner lotion, a beauty essence serum, a facial pack, a carmine lotion, a liquid face wash, a face wash foam, a face wash cream, a face wash powder, a makeup cleansing, a body gloss, a sunscreen or suntan cream or lotion, a water-based suncut lotion, and an O/W-type sunscreen cosmetic. Examples of the hair cosmetic include a hair gloss, a hair cream, a hair shampoo, a hair rinse, a hair color, a hair brushing agent, and a hair treatment. Examples of an antiperspirant include cream, lotion, powder, and spray-type deodorant products. In addition, a milky lotion, a soap, a bathing agent, a perfume, and the like are also included in the cosmetic in the present application.

EXAMPLES

Hereinafter, the present invention will be described in detail with reference to preferred Examples and Comparative Examples corresponding to the Examples. The present invention is not limited to the following Examples, and modification, change, application (including partial one) and combination thereof can be made without deviating from the technical meaning of the present invention found from the following Examples.

[Evaluation of Hydrophilicity and Ductility and Adhesion of Hydrophilized Organic Powder]

First, hydrophilized organic powders shown in the following Examples 1 to 6 and Comparative Examples 1 to 7 were prepared, and the hydrophilicity and the ductility and adhesion of each powder were evaluated.

Example 1

45.7 g of polyoxyethylene (10) isostearyl ether (Nonion IS-210) was added to 1.6 kg of ion exchanged water and dissolved in a white turbid state at 60° C. The resulting solution was added to 3 kg of a silicone powder (trade name: KSP-100 (Shin-Etsu Chemical Co., Ltd.)), kneaded with a kneader mixer for 15 minutes, and then vacuum-heated with stirring, whereby a hydrophilized silicone powder was obtained. The hydrophilized silicone powder has a hydrophilizing-coat formed of polyoxyethylene (10) isostearyl ether. With respect to the hydrophilizing-coat, the same applies to the following Examples.

Example 2

40 g of polyoxyethylene (10) isostearyl ether (Nonion IS-210) was added to 200 g of an ion exchanged water/isopropyl alcohol (IPA)=8/2 (wt %) solution and dissolved therein. 4 kg of lauroyl lysine (trade name: Amihope LL (Ajinomoto Healthy Supply Co., Ltd.) was put in a heater Henschel and stirred for 15 minutes. Heated steam was allowed to pass through the jacket of the heater Henschel and ion exchanged water and IPA were distilled off by heating with stirring. The resultant was pulverized with an atomizer, whereby a hydrophilized amino acid powder was obtained.

Example 3

30 g of polyoxyethylene (10) isostearyl ether (Nonion IS-210) was added to 3 kg of ion exchanged water and dissolved in a white turbid state at 60° C. While stirring the resulting solution using a disper mixer, 3 kg of a silicone powder (trade name: KSP-102 (Shin-Etsu Chemical Co., Ltd.)) was gradually added thereto and dispersed in the aqueous layer. From the resulting dispersion liquid, water was removed in an atmosphere of 160° C. with a two-fluid nozzle spray-type spray dryer, whereby a hydrophilized silicone powder was obtained.

Example 4

3 kg of a polyurethane powder (trade name: DAIMIC BEAZ UCN-8070CM (Dainichiseika Color & Chemicals Mfg. Co., Ltd.)) was treated in the same manner as the method of Example 1 except that the solvent was changed to ion exchanged water/IPA=8/2 (wt %), whereby a hydrophilized polyurethane powder was obtained.

Example 5

3 kg of a metallic soap fine powder (trade name: Calcium Stearate S (NOF Corporation)) was treated in the same manner as the method of Example 4, whereby a hydrophilized metallic soap powder was obtained.

Example 6

4 kg of a silicone powder (trade name: KMP-591 (Shin-Etsu Chemical Co., Ltd.)) was treated in the same manner as the method of Example 2, whereby a hydrophilized silicone powder was obtained.

Comparative Example 1

The polyoxyethylene (10) isostearyl ether in Example 1 was changed to polyoxyethylene (15) isostearyl ether (EMALEX 1815) and a treatment was performed in the same manner, whereby a hydrophilized silicone powder was obtained. The hydrophilized silicone powder has a hydrophilizing-coat formed of polyoxyethylene (15) isostearyl ether. With respect to the hydrophilizing-coat, the same applies to the following Comparative Examples.

Comparative Example 2

The polyoxyethylene (10) isostearyl ether in Example 1 was changed to polyoxyethylene (5) isostearyl ether (EMALEX 1805) and a treatment was performed in the same manner, whereby a hydrophilized silicone powder was obtained.

Comparative Example 3

The polyoxyethylene (10) isostearyl ether in Example 2 was changed to polyoxyethylene (15) isostearyl ether (EMALEX 1815) and a treatment was performed in the same manner, whereby a hydrophilized lauroyl lysine was obtained.

Comparative Example 4

The polyoxyethylene (10) isostearyl ether in Example 3 was changed to polyoxyethylene (15) isostearyl ether (EMALEX 1815) and a treatment was performed in the same manner, whereby a hydrophilized silicone powder was obtained.

Comparative Example 5

The polyoxyethylene (10) isostearyl ether in Example 4 was changed to polyoxyethylene (15) isostearyl ether (EMALEX 1815) and a treatment was performed in the same manner, whereby a hydrophilized polyurethane powder was obtained.

Comparative Example 6

The polyoxyethylene (10) isostearyl ether in Example 5 was changed to polyoxyethylene (15) isostearyl ether (EMALEX 1815) and a treatment was performed in the same manner, whereby a hydrophilized metallic soap powder was obtained.

Comparative Example 7

A hydrophilized silicone powder was obtained by performing a treatment in the same manner except that the silicone resin described in Production Example 6 of WO 2007/007521 was changed to a silicone powder (trade name: KMP-591 (Shin-Etsu Chemical Co., Ltd.)).

(Evaluation Method for Hydrophilicity)

Ion exchanged water and a hydrophilized organic powder (0.3 g) were placed in a 50 cc glass vial, and the vial was vigorously shaken 10 times and then left for 1 minute, and the dispersibility in water (that is, hydrophilicity) was observed. In addition, after 24 hours, the state of dispersion in water was observed in the same manner.

(Evaluation Criteria for Hydrophilicity after 1 Minute)

A: All the powder is dispersed in the aqueous layer to cause strong white turbidity, and few bubbles are formed.

C: Most of the powder is dispersed in the aqueous layer to cause white turbidity, but many bubbles are formed and the powder is slightly observed at the gas-liquid interface.

FIG. 1 shows evaluation examples (Example 6: A, Comparative Example 3: C) according to the evaluation criteria after 1 minute.

(Evaluation Criteria for Hydrophilicity after 24 Hours)

A: The powder is dispersed in the aqueous layer.

C: The powder is not dispersed in the aqueous layer, but floats or precipitates.

Figure 2:
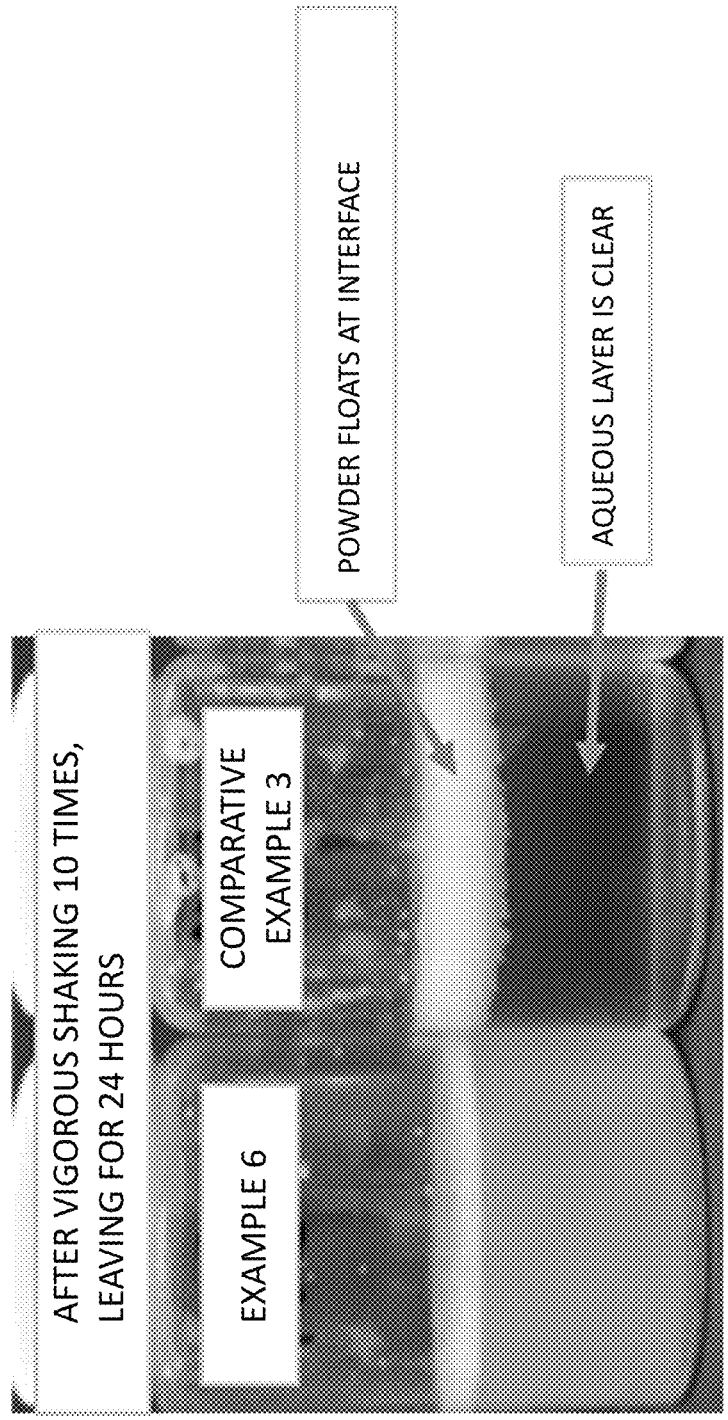
FIG. 2 shows an example of an evaluation result of the hydrophilicity of a hydrophilized organic powder of the present invention.

FIG. 2 shows evaluation examples (Example 6: A, Comparative Example 3: C) according to the evaluation criteria after 24 hours.

(Evaluation Method for Ductility and Adhesion)

A 25 cm (vertical length)×10 cm (horizontal length) piece of artificial leather (manufactured by Idemitsu Chemicals Co., Ltd., trade name: Saplare) was set on an automatic coating device (Tester Sangyo Co., Ltd.). 0.3 g of each treated powder was placed on the horizontal edge of the artificial leather, and subsequently, a flat indenter with a sponge puff attached thereto was placed on the powder. The coating degree of the powder on the artificial leather when the flat indenter was moved on the artificial leather under the condition of 200 mm at a moving speed of 35 mm/sec was observed, and the ductility and adhesion state of the powder was evaluated on a three-point scale.

(Evaluation Criteria for Ductility and Adhesion)

A: A powder coat is uniformly formed on the artificial leather over the entire movement distance of the sponge puff.

B: The coat is uneven.

C: Coating could hardly be achieved.

Figure 3:
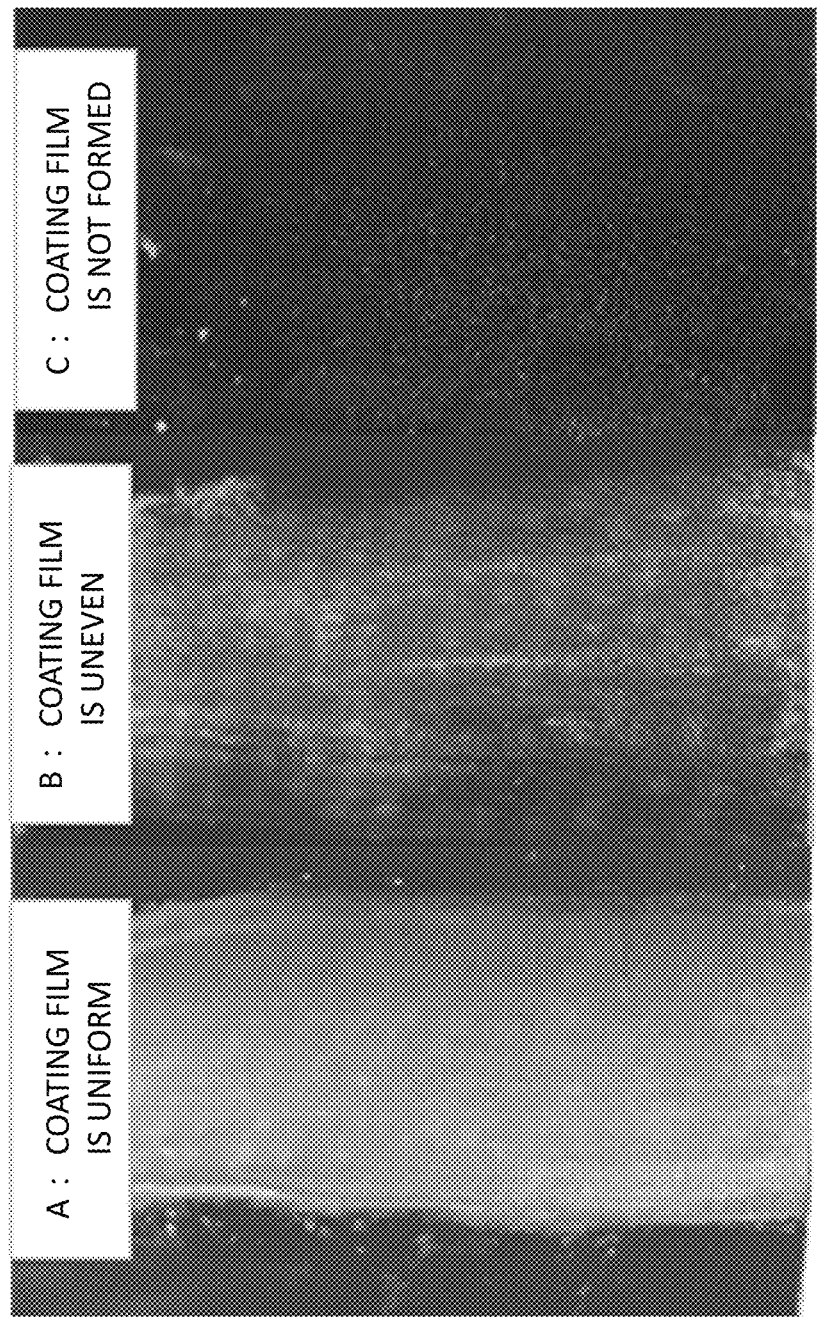
FIG. 3 shows an example of an evaluation result of the ductility and adhesion of a hydrophilized organic powder of the present invention.

FIG. 3 shows evaluation examples (A, B, and C) according to the evaluation criteria for the ductility and adhesion.

(Evaluation Results of Hydrophilicity and Ductility and Adhesion)

TABLE 1

| | Hydrophilicity | | Ductility and adhesion |
|---|---|---|---|
| | After 1 minute | After 24 hours | |
| Example 1 | A | A | A |
| Example 2 | A | A | A |
| Example 3 | A | A | A |
| Example 4 | A | A | A |
| Example 5 | A | A | A |
| Example 6 | A | A | A |
| Comparative Example 1 | C | C | C |
| Comparative Example 2 | C | C | B |
| Comparative Example 3 | C | C | C |
| Comparative Example 4 | C | C | C |

TABLE 1-continued

| | Hydrophilicity | | Ductility and adhesion |
|---|---|---|---|
| | After 1 minute | After 24 hours | |
| Comparative Example 5 | C | C | C |
| Comparative Example 6 | C | C | C |
| Comparative Example 7 | C | C | C |

From the evaluation results of Example 1 and Comparative Examples 1 and 2, it was found that when the silicone powder is hydrophilized with polyoxyethylene isostearyl ether, the optimum number of moles added of polyoxyethylene is 10 in terms of hydrophilicity and ductility and adhesion. That is, it was found that the hydrophilicity and the ductility and adhesion are deteriorated if the number of moles added of ethylene oxide is less than 10 (particularly the number of moles added in Comparative Example 2: 5) or more than 10 (particularly the number of moles added in Comparative Example 3: 15) as compared with the case where the number of moles added is 10.

Further, from the evaluation results of Examples 2, 4, 5, and 6, it was found that the usefulness of polyoxyethylene (10) isostearyl ether is achieved independently of the type of solvent or the type of hydrophobic organic powder.

Further, from the evaluation results of Example 3, it was found that the usefulness of polyoxyethylene (10) isostearyl ether is achieved independently of the preparation method for the hydrophilized organic powder.

It was found that the hydrophilized organic powders of Examples 1 to 6 have useful properties in terms of hydrophilicity and ductility and adhesion as compared with the known technology (Comparative Example 7).

Further, since the hydrophilized silicone powder or the hydrophilized polyurethane powder has a specific gravity less than 1.0, even if the powder is once dispersed in water, it floats on the surface of water with the passage of time due to the difference in specific gravity between solid and liquid, but it was found that in the hydrophilized organic powder treated with polyoxyethylene (10) isostearyl ether, such tendency is suppressed (see FIGS. 1 and 2). Further, since the hydrophilized metallic soap powder has a specific gravity of 1.0 or more, it precipitates in water with the passage of time, however, it was found that in the hydrophilized organic powder treated with polyoxyethylene (10) isostearyl ether, such tendency is suppressed.

[Evaluation of State Immediately after Dispersion, Stability Over Time, and Sense of Use of Aqueous Dispersion]

Aqueous dispersions shown in the following Examples 7 to 10 and Comparative Examples 8 to 10 were prepared, and with respect to each aqueous dispersion, the state immediately after dispersion, the stability over time after 7 days at 50° C., and the sense of use were evaluated. Each aqueous dispersion was prepared using a homomixer according to the formulation shown in Table 2.

(Evaluation Criteria for State Immediately after Dispersion)

A: The dispersion has a smooth appearance and fluidity.

C: An aggregate is observed and the dispersion does not flow.

(Evaluation Criteria for Stability Over Time)

A: The dispersion has a smooth appearance and fluidity, and liquid separation or floating does not occur.

C: The powder layer is floating and a clear layer is observed in the lower layer.

(Evaluation Criteria for Sense of Use)
  A: The dispersion is smooth and spreads well.
  B: The dispersion is slightly smooth and spreads well.
  C: The dispersion is slightly sticky and feels heavy.
(Evaluation Results of State Immediately after Dispersion, Stability Over Time, and Sense of Use)

isostearyl ether (that is, the powder of Comparative Example 1) and the hydrophilized silicone powder treated with polyoxyethylene (5) isostearyl ether (that is, the powder of Comparative Example 2) cannot achieve the desired property in terms of the state immediately after dispersion and the sense of use.

TABLE 2

|  | Example 7 | Example 8 | Example 9 | Example 10 | Comparative Example 8 | Comparative Example 9 | Comparative Example 10 |
|---|---|---|---|---|---|---|---|
| Powder of Example 1 | 53 g | 53 g | — | — | — | — | — |
| Powder of Comparative Example 1 | — | — | — | — | 53 g | — | — |
| Powder of Comparative Example 2 | — | — | — | — | — | 53 g | 53 g |
| KSP-100 | — | — | 53 g | 53 g | — | — | — |
| Nonion IS-210 | — | — | 0.8 g | 0.8 g | — | — | — |
| BG | 5.0 g | 5.0 g | 5.0 g | 5.0 g | 5.0 g | 5.0 g | 5.0 g |
| Phenoxyethanol | 0.5 g | 0.5 g | 0.5 g | 0.5 g | 0.5 g | 0.5 g | 0.5 g |
| SEPINOV P88 | — | 0.3 g | — | 0.3 g | — | — | 0.3 g |
| Ion exchanged water | balance | balance | balance | balance | balance | balance | balance |
| State immediately after dispersion | A | A | A | A | C | C | C |
| Dispersion stability (50° C./7 days) | C | A | C | A | C | C | C |
| Sense of use of organic powder | A | A | B | B | B | C | C |

From the evaluation results of Example 7, it was found that even if the hydrophilized silicone powder treated with polyoxyethylene (10) isostearyl ether (that is, the powder of Example 1) is prepared in a state of an aqueous dispersion containing BG (butylene glycol: moisturizer) and phenoxyethanol (preservative), the state immediately after dispersion is favorable, and also a good sense of use is obtained.

In addition, from the evaluation results of Example 8, it was found that when SEPINOV 88 (thickener) is further blended, the stability over time is improved. That is, by preparing an aqueous dispersion as a material of a cosmetic, an advantage that scattering of the hydrophilized organic powder when producing a cosmetic can be suppressed, or an advantage that the hydrophilized organic powder can be prevented from aggregating is obtained, however, in order to obtain such an advantage, the hydrophilized organic powder is required to have a property of being stably dispersed in water over time. Here, it is considered that the hydrophilized organic powder of the present invention does not require the addition of other components such as a dispersant because the stability over time is improved by using the thickener.

Further, from the evaluation results of Examples 9 and 10, it was found that when a silicone powder (KSP-100) and polyoxyethylene (10) isostearyl ether (Nonion IS-210) were separately blended in the aqueous dispersion, the state immediately after dispersion is favorable, and the sense of use is generally good, although it is slightly poorer than in the case where it is prepared in a state of a hydrophilized silicone powder.

On the other hand, from the evaluation results of Comparative Examples 8 and 9, it was found that the hydrophilized silicone powder treated with polyoxyethylene (15)

[Evaluation of Sense of Use, Cosmetic Effect, and Cosmetic Durability of Powder Foundation]

Powder foundations having a composition shown in either of the following Example 11 and Comparative Example 11 were prepared, and the sense of use, cosmetic effect, and cosmetic durability of each powder foundation were evaluated.

(Preparation Method for Powder Foundation)
  A: The powder components were well dispersed and mixed.
  B: The oily components were well mixed and dissolved.
  C: After B was added to A, the resultant was mixed and pulverized, and then allowed to pass through a sieve and compression-molded in a metal plate, whereby a powder foundation was obtained.

(Evaluation Methods for Sense of Use, Cosmetic Effect, and Cosmetic Durability)

The sense of use, cosmetic effect, and cosmetic durability were evaluated based on the average of scores given by 25 expert panelists who were asked to use each powder foundation for one day and score on a five-point scale shown below. The sense of use was evaluated in terms of good smoothness, no stickiness, and comfort. Further, the cosmetic effect is evaluated in terms of powderiness, no uneven coating, uniformity of the cosmetic coat, and natural luster. Further, the cosmetic durability is evaluated in terms of occurrence of color dullness or shininess with the passage of time, and no powder aggregation.

(Evaluation Criteria)
  Evaluation result: score
  Very good: 5 points
  Good: 4 points
  Average: 3 points
  Slightly poor: 2 points
  Poor: 1 point

TABLE 3

| | Components | Example 11 | Comparative Example 11 |
|---|---|---|---|
| Powder components | Hydrophobic stearic acid-treated fine particle zinc oxide | 6.0 (wt %) | 6.0 (wt %) |
| | Hydrophobic silicone-treated sericite | 25.0 | 25.0 |
| | Hydrophobic silicone-treated mica | 10.0 | 10.0 |
| | Spherical silica | 5.0 | 5.0 |
| | Hydrophobic lecithin-treated titanium oxide | 8.5 | 8.5 |
| | Hydrophobic lecithin-treated yellow iron oxide | 3.1 | 3.1 |
| | Hydrophobic lecithin-treated red iron oxide | 2.0 | 2.0 |
| | Hydrophobic lecithin-treated black iron oxide | 0.3 | 0.3 |
| | Powder of Example 2 | 6.0 | — |
| | Powder of Comparative Example 3 | — | 6.0 |
| | Powder of Example 5 | 4.0 | — |
| | Powder of Comparative Example 6 | — | 4.0 |
| | Hydrophobic silicone-treated talc | balance | balance |
| Oily components | 2-Ethylhexyl p-methoxycinnamate | 3.0 | 3.0 |
| | Glyceryl tri-2-ethylhexanoate | 2.0 | 2.0 |
| | Dimethylpolysiloxane (20 cs) | 3.0 | 3.0 |
| | Squalene | 3.0 | 3.0 |
| | Sorbitan sesquistearate | 0.5 | 0.5 |
| | Antibacterial agent | q.s. | q.s. |
| | Antioxidant | q.s. | q.s. |
| Evaluation results | Sense of use | 4.7 | 4.0 |
| | Cosmetic effect | 4.7 | 3.8 |
| | Cosmetic durability | 3.9 | 3.3 |

From the evaluation results of Example 11, it was found that even if the hydrophilized amino acid powder treated with polyoxyethylene (10) isostearyl ether (that is, the powder of Example 2) and the hydrophilized metallic soap powder treated with polyoxyethylene (10) isostearyl ether (that is, the powder of Example 5) are prepared into a powder foundation, good sense of use, cosmetic effect, and cosmetic durability are obtained.

On the other hand, from the evaluation results of Comparative Example 11, it was found that when the hydrophilized amino acid powder treated with polyoxyethylene (15) isostearyl ether (that is, the powder of Comparative Example 3) and the hydrophilized metallic soap powder treated with polyoxyethylene (15) isostearyl ether (that is, the powder of Comparative Example 6) are prepared into a powder foundation, the sense of use, cosmetic effect, and cosmetic durability are poorer than in the case where one treated with polyoxyethylene (10) isostearyl ether is used (that is, Example 11).

[Evaluation of Sense of Use, Cosmetic Effect, and Cosmetic Durability of Oily Solid Foundation]

Oily solid foundations having a composition shown in either of the following Example 12 and Comparative Example 12 were prepared, and the sense of use, cosmetic effect, and cosmetic durability of each oily solid foundation were evaluated.

(Preparation Method for Oily Solid Foundation)

A: The powder components were well dispersed and mixed.

B: The oily components were well mixed and dissolved.

C: After B was added to A, the resultant was treated with a heat roller, and poured into a metal plate, and then cooled and molded, whereby an oily solid foundation was obtained.

(Evaluation Methods for Sense of Use, Cosmetic Effect, and Cosmetic Durability)

The sense of use, cosmetic effect, and cosmetic durability of the oily solid foundation were evaluated in the same manner as the above-mentioned powder foundation.

TABLE 4

| | Components | Example 12 | Comparative Example 12 |
|---|---|---|---|
| Oily components | Polyglyceryl-2 triisostearate | 8.5 (wt %) | 8.5 (wt %) |
| | Propylene glycol dicaprate | 10.0 | 10.0 |
| | Dimethylpolysiloxane (20 cs) | 9.0 | 9.0 |
| | (Dimethicone/vinyl dimethicone) crosspolymer | 5.0 | 5.0 |
| | Petrolatum | 7.5 | 7.5 |
| | Polyethylene wax | 4.0 | 4.0 |
| | Candelilla wax | 1.5 | 1.5 |
| | 2-Ethylhexyl p-methoxycinnamate | 3.0 | 3.0 |
| Powder components | Acylated amino acid-treated talc | balance | balance |
| | Powder of Example 1 | 6.0 | — |
| | Powder of Comparative Example 1 | — | 6.0 |
| | Powder of Example 2 | 5.0 | — |
| | Powder of Comparative Example 3 | — | 5.0 |
| | Hydrophobic silicone-treated titanium oxide | 5.0 | 5.0 |
| | Hydrophobic silicone-treated yellow iron oxide | 2.2 | 2.2 |
| | Hydrophobic silicone-treated red iron oxide | 1.0 | 1.0 |
| | Hydrophobic silicone-treated black iron oxide | 0.2 | 0.2 |
| | Preservative | q.s. | q.s. |
| Evaluation results | Sense of use | 4.8 | 4.1 |
| | Cosmetic effect | 4.9 | 4.0 |
| | Cosmetic durability | 4.5 | 4.0 |

From the evaluation results of Example 12, it was found that even if the hydrophilized silicone powders treated with polyoxyethylene (10) isostearyl ether (that is, the powders of Examples 1 and 2) are prepared into an oily solid foundation, good sense of use, cosmetic effect, and cosmetic durability are obtained.

On the other hand, from the evaluation results of Comparative Example 12, it was found that when the hydrophilized silicone powders treated with polyoxyethylene (15) isostearyl ether (that is, the powders of Comparative Examples 1 and 3) are prepared into an oily solid foundation, the sense of use, cosmetic effect, and cosmetic durability are poorer than in the case where one treated with polyoxyethylene (10) isostearyl ether is used (that is, Example 12).

[Evaluation of Sense of Use, Cosmetic Effect, and Cosmetic Durability of W/O-Type Emulsion Foundation]

W/O-type emulsion foundations having a composition shown in any of the following Examples 13 and 14 and Comparative Examples 13 and 14 were prepared, and the sense of use, cosmetic effect, and cosmetic durability of each W/O-type emulsion foundation were evaluated.

(Preparation Method for W/O-Type Emulsion Foundation)

A: The oil layer components were well dispersed and mixed.

B: The aqueous layer components were well dispersed and mixed.

C: After B was added to A, the resultant was emulsified with a homomixer, whereby a W/O-type emulsion foundation was obtained.

(Evaluation Methods for Sense of Use, Cosmetic Effect, and Cosmetic Durability)

The sense of use, cosmetic effect, and cosmetic durability of the W/O-type emulsion foundation were evaluated in the same manner as the above-mentioned powder foundation.

TABLE 5

| | Components | Example 13 | Comparative Example 13 |
|---|---|---|---|
| Oil layer components | Decamethylcyclopentasiloxane | 10.0 (wt %) | 10.0 (wt %) |
| | Isododecane | 7.0 | 7.0 |
| | Triethylhexanoin | 5.0 | 5.0 |
| | PEG-10 dimethicone | 3.5 | 3.5 |
| | Alkyl silane-treated fine particle zinc oxide | 6.5 | 6.5 |
| | Hydrophobic silicone-treated titanium oxide | 7.5 | 7.5 |
| | Hydrophobic silicone-treated yellow iron oxide | 3.0 | 3.0 |
| | Hydrophobic silicone-treated red iron oxide | 1.2 | 1.2 |
| | Hydrophobic silicone-treated black iron oxide | 0.3 | 0.3 |
| Aqueous layer components | Powder of Example 1 | 8.0 | — |
| | Powder of Comparative Example 1 | — | 8.0 |
| | BG | 6.0 | 6.0 |
| | Phenoxyethanol | 0.8 | 0.8 |
| | Ion exchanged water | to 100.0 | to 100.0 |
| Evaluation results | Sense of use | 4.3 | 3.7 |
| | Cosmetic effect | 4.5 | 3.8 |
| | Cosmetic durability | 3.4 | 3.2 |

TABLE 6

| | Components | Example 14 | Comparative Example 14 |
|---|---|---|---|
| Oil layer components | Isohexadecane | 13.0 (wt %) | 13.0 (wt %) |
| | Glyceryl tri-2-ethylhexanoate | 5.5 | 5.5 |
| | 2-Ethylhexyl p-methoxycinnamate | 5.0 | 5.0 |
| | PEG-9 dimethicone | 2.0 | 2.0 |
| | Hydrophobic alkyl silane-treated titanium oxide | 8.0 | 8.0 |
| | Hydrophobic alkyl silane-treated yellow iron oxide | 2.8 | 2.8 |
| | Hydrophobic alkyl silane-treated red iron oxide | 1.1 | 1.1 |
| | Hydrophobic alkyl silane-treated black iron oxide | 0.2 | 0.2 |
| Aqueous layer components | BG | 8.0 | 8.0 |
| | Powder of Example 2 | 8.0 | — |
| | Powder of Comparative Example 3 | — | 8.0 |
| | Carbomer | 0.3 | 0.3 |
| | Triethanolamine | 0.15 | 0.15 |
| | Phenoxyethanol | 0.5 | 0.5 |
| | Ion exchanged water | balance | balance |
| Evaluation results | Sense of use | 4.8 | 3.9 |
| | Cosmetic effect | 4.6 | 3.9 |
| | Cosmetic durability | 3.8 | 3.6 |

From the evaluation results of Examples 13 and 14, it was found that even if the hydrophilized silicone powders treated with polyoxyethylene (10) isostearyl ether (that is, the powders of Examples 1 and 2) are each prepared into a W/O-type emulsion foundation, good sense of use, cosmetic effect, and cosmetic durability are obtained. In addition, it was found that the W/O-type emulsion foundation including the hydrophilized silicone powder treated with polyoxyethylene (10) isostearyl ether can achieve good sense of use, cosmetic effect, and cosmetic durability independently of the oil layer components and the aqueous layer components.

On the other hand, from the evaluation results of Comparative Examples 13 and 14, it was found that when the hydrophilized silicone powders treated with polyoxyethylene (15) isostearyl ether (that is, the powders of Comparative Examples 1 and 3) are each prepared into a W/O-type emulsion foundation, the sense of use, cosmetic effect, and cosmetic durability are poorer than in the case where one treated with polyoxyethylene (10) isostearyl ether is used (that is, Examples 13 and 14).

[Evaluation of Cosmetic Effect of Water-Based Suncut Lotion]

Water-based suncut lotions having a composition shown in either of the following Example 15 and Comparative Example 15 were prepared, and the cosmetic effect of each water-based suncut lotion was evaluated.

(Preparation Method for Water-Based Suncut Lotion)

A: The oil layer components were well dispersed and mixed.

B: The aqueous layer components were well dispersed and mixed.

C: After A was added to B, the resultant was emulsified with a homomixer, whereby a water-based suncut lotion was obtained.

(Evaluation Method for Cosmetic Effect)

The cosmetic effect was evaluated in the same manner as the above-mentioned powder foundation in terms of stickiness, oily sensation, and comfort.

TABLE 7

| | Components | Example 15 | Comparative Example 15 |
|---|---|---|---|
| Oil layer components | Decamethylcyclopentasiloxane | 12.0 (wt %) | 12.0 (wt %) |
| | Dimethylpolysiloxane (6 cs) | 6.0 | 6.0 |
| | Isotridecyl isononanoate | 5.0 | 5.0 |
| | 2-Ethylhexyl p-methoxycinnamate | 7.0 | 7.0 |
| | PEG-9 polydimethylsiloxyethyl dimethicone | 2.0 | 2.0 |
| | (Dimethicone/PEG-10/15) crosspolymer | 2.0 | 2.0 |
| | Hydrophobic stearic acid-treated fine particle titanium oxide | 10.0 | 10.0 |
| Aqueous layer components | Powder of Example 4 | 8.0 | — |
| | Powder of Comparative Example 5 | — | 8.0 |
| | 1,3-BG | 5.0 | 5.0 |
| | Ethanol | 5.0 | 5.0 |
| | Purified water | balance | balance |
| Evaluation results | No stickiness | 4.5 | 3.7 |
| | No oily sensation | 4.7 | 3.3 |
| | Comfort | 4.5 | 3.5 |

From the evaluation results of Example 15, it was found that even if the hydrophilized polyurethane powder treated with polyoxyethylene (10) isostearyl ether (that is, the powder of Example 4) is prepared into a water-based suncut lotion, a good cosmetic effect, that is, no stickiness, no oily sensation, and comfort are obtained.

On the other hand, from the evaluation results of Comparative Example 15, it was found that when the hydrophilized polyurethane powder treated with polyoxyethylene (15) isostearyl ether (that is, the powder of Comparative Example 5) is prepared into a water-based suncut lotion, the cosmetic effect is poorer than in the case where one treated with polyoxyethylene (10) isostearyl ether is used (that is, Example 15).

[Evaluation of Cosmetic Effect of O/W-Type Sunscreen Cosmetic]

O/W-type sunscreen cosmetics having a composition shown in any of the following Examples 16 and 17 and Comparative Examples 16 and 17 were prepared, and the cosmetic effect of each 0/W-type sunscreen cosmetic was evaluated.

(Preparation Method for 0/W-Type Sunscreen Cosmetic)

A: The oil layer components were well dispersed and mixed.

B: The aqueous layer components were well dispersed and mixed.

C: After A was added to B, the resultant was emulsified with a homomixer, whereby an O/W-type sunscreen cosmetic was obtained.

(Evaluation Method for Cosmetic Effect)

The cosmetic effect, that is, stickiness, oily sensation, and comfort were evaluated in the same manner as the above-mentioned water-based suncut lotion.

TABLE 8

| | Components | Example 16 | Comparative Example 16 |
|---|---|---|---|
| Oil layer components | Decamethylcyclopentasiloxane | 10.0 (wt %) | 10.0 (wt %) |
| | Isododecane | 10.0 | 10.0 |
| | Diisopropyl sebacate | 8.0 | 8.0 |
| | PEG-10 dimethicone | 4.0 | 4.0 |
| | Diethylamino hydroxybenzoyl hexyl benzoate | 8.0 | 8.0 |
| | Surface-treated fine particle titanium oxide | 7.0 | 7.0 |
| | Surface-treated fine particle zinc oxide | 12.0 | 12.0 |
| Aqueous layer components | Powder of Example 1 | 5.0 | — |
| | Powder of Comparative Example 1 | — | 5.0 |
| | Powder of Example 4 | 5.0 | — |
| | Powder of Comparative Example 5 | — | 5.0 |
| | BG | 10.0 | 10.0 |
| | Phenoxyethanol | 0.5 | 0.5 |
| | Purified water | balance | balance |
| Evaluation results | No stickiness | 4.5 | 3.7 |
| | No oily sensation | 4.7 | 3.3 |
| | Comfort | 4.5 | 3.5 |

TABLE 9

| | Components | Example 17 | Comparative Example 17 |
|---|---|---|---|
| Oil layer components | Isohexadecane | 8.0 | 8.0 |
| | Tridecyl isononanoate | 5.0 | 5.0 |
| | Dimethylpolysiloxane (10 cs) | 3.0 | 3.0 |
| | Cetostearyl alcohol | 1.5 | 1.5 |
| | 2-Ethylhexyl p-methoxycinnamate | 8.0 | 8.0 |
| Aqueous layer components | Powder of Example 4 | 7.0 | — |
| | Powder of Comparative Example 5 | — | 7.0 |
| | PEG-80 hydrogenated castor oil | 2.0 | 2.0 |
| | Acrylate/sodium acryloyldimethyltaurate copolymer | 0.5 | 0.5 |

TABLE 9-continued

| | Components | Example 17 | Comparative Example 17 |
|---|---|---|---|
| | Xanthan gum | 0.1 | 0.1 |
| | Methyl paraoxybenzoate | q.s. | q.s. |
| | Glycerin | 6.0 | 6.0 |
| | Ethanol | 5.0 | 5.0 |
| | Purified water | balance | balance |
| Evaluation results | No stickiness | 4.6 | 3.9 |
| | No oily sensation | 4.5 | 3.8 |
| | Comfort | 4.3 | 3.8 |

From the evaluation results of Examples 16 and 17, it was found that even if the hydrophilized silicone powder treated with polyoxyethylene (10) isostearyl ether (that is, the powder of Example 1) and the hydrophilized polyurethane powder treated with polyoxyethylene (10) isostearyl ether (that is, the powder of Example 4) are each prepared into an O/W-type sunscreen cosmetic, a good cosmetic effect, that is, no stickiness, no oily sensation, and comfort are obtained. In addition, it was found that the O/W-type sunscreen cosmetic including the hydrophilized powder treated with polyoxyethylene (10) isostearyl ether can achieve a good cosmetic effect independently of the oil layer components and the aqueous layer components.

On the other hand, from the evaluation results of Comparative Examples 16 and 17, it was found that when the hydrophilized silicone powder treated with polyoxyethylene (15) isostearyl ether (that is, the powder of Comparative Example 1) and the hydrophilized polyurethane powder treated with polyoxyethylene (15) isostearyl ether (that is, the powder of Comparative Example 5) are each prepared into an O/W-type sunscreen cosmetic, the cosmetic effect is poorer than in the case where one treated with polyoxyethylene (10) isostearyl ether is used (that is, Examples 16 and 17).

[Evaluation of Sense of Use, Cosmetic Effect, and Cosmetic Durability of Water-Based White Powder Foundation]

Water-based white powder foundations having a composition shown in any of the following Example 18 and Comparative Examples 18 and 19 were prepared, and the sense of use, cosmetic effect, and cosmetic durability of each water-based white powder foundation were evaluated.

(Preparation Method for Water-Based White Powder Foundation)

A: The powder components were well mixed.

B: The aqueous layer components were mixed and dissolved.

C: After A was added to B, the resultant was well stirred, whereby a water-based white powder foundation was obtained.

(Evaluation Methods for Sense of Use, Cosmetic Effect, and Cosmetic Durability)

The sense of use, cosmetic effect, and cosmetic durability of the water-based white powder foundation were evaluated in the same manner as the above-mentioned powder foundation.

TABLE 10

| | Components | Example 18 | Comparative Example 18 | Comparative Example 19 |
|---|---|---|---|---|
| Powder components | Talc | 10.0 (wt %) | 10.0 (wt %) | 10.0 (wt %) |
| | Boron nitride | 3.0 | 3.0 | 3.0 |
| | Synthetic mica | 3.5 | 3.5 | 3.5 |
| | Powder of Example 1 | 7.0 | — | — |
| | Powder of Comparative Example 1 | — | 7.0 | — |
| | Powder of Comparative Example 2 | — | — | 7.0 |
| Aqueous layer components | BG | 5.0 | 5.0 | 5.0 |
| | Glycerin | 5.0 | 5.0 | 5.0 |
| | Ethanol | 5.0 | 5.0 | 5.0 |
| | EDTA•2Na | 0.2 | 0.2 | 0.2 |
| | Phenoxyethanol | 0.3 | 0.3 | 0.3 |
| | SEPIMAX ZEN | 0.2 | 0.2 | 0.2 |
| | Ion exchanged water | balance | balance | balance |
| Evaluation results | Sense of use | 4.2 | 3.3 | 3.8 |
| | Cosmetic effect | 4.1 | 3.1 | 3.7 |
| | Cosmetic durability | 3.5 | 3.0 | 3.3 |

From the evaluation results of Example 18, it was found that even if the hydrophilized silicone powder treated with polyoxyethylene (10) isostearyl ether (that is, the powder of Example 1) is prepared into a water-based white powder foundation, good sense of use, cosmetic effect, and cosmetic durability are obtained.

On the other hand, from the evaluation results of Comparative Example 18, it was found that when the hydrophilized silicone powder treated with polyoxyethylene (15) isostearyl ether (that is, the powder of Comparative Example 1) is prepared into a water-based white powder foundation, the sense of use, cosmetic effect, and cosmetic durability are poorer than in the case where one treated with polyoxyethylene (10) isostearyl ether is used (that is, Example 18). In addition, from the evaluation results of Comparative Example 19, it was found that also the water-based white powder foundation including the hydrophilized silicone powder treated with polyoxyethylene (5) isostearyl ether (that is, the powder of Comparative Example 2) has poor sense of use, cosmetic effect, and cosmetic durability.

[Evaluation of Sense of Use, Cosmetic Effect, and Cosmetic Durability of Water-Based Eye Shadow]

Water-based eye shadows having a composition shown in either of the following Example 19 and Comparative Example 20 were prepared, and the sense of use, cosmetic effect, and cosmetic durability of each water-based eye shadow were evaluated.

(Preparation Method for Water-Based Eye Shadow)
(Production Method)

A: The powder components were well mixed.

B: The aqueous layer components were mixed and dissolved.

C: After A was added to B, the resultant was well stirred, whereby a water-based eye shadow was obtained.

(Evaluation Methods for Sense of Use, Cosmetic Effect, and Cosmetic Durability)

The sense of use, cosmetic effect, and cosmetic durability of the water-based eye shadow were evaluated in the same manner as the above-mentioned powder foundation.

TABLE 11

| | Components | Example 19 | Comparative Example 20 |
|---|---|---|---|
| Powder components | Talc | 5.0 (wt %) | 5.0 (wt %) |
| | Pearl pigment | 18.0 | 18.0 |
| | Yellow iron oxide | 0.8 | 0.8 |
| | Red iron oxide | 0.2 | 0.2 |
| | Black iron oxide | 0.1 | 0.1 |
| | Powder of Example 5 | 5.0 | — |
| | Powder of Comparative Example 6 | — | 5.0 |
| Aqueous layer components | BG | 5.0 | 5.0 |
| | Glycerin | 5.0 | 5.0 |
| | Ethanol | 5.0 | 5.0 |
| | EDTA•2Na | 0.2 | 0.2 |
| | Citric acid | 0.03 | 0.03 |
| | Sodium citrate | 0.12 | 0.12 |
| | Phenoxyethanol | 0.3 | 0.3 |
| | SEPINOV P88 | 0.2 | 0.2 |
| | Ion exchanged water | balance | balance |
| Evaluation results | Sense of use | 4.5 | 3.2 |
| | Cosmetic effect | 4.3 | 3.8 |
| | Cosmetic durability | 3.7 | 3.2 |

From the evaluation results of Example 19, it was found that even if the hydrophilized metallic soap powder treated with polyoxyethylene (10) isostearyl ether (that is, the powder of Example 5) is prepared into a water-based eye shadow, good sense of use, cosmetic effect, and cosmetic durability are obtained.

On the other hand, from the evaluation results of Comparative Example 20, it was found that when the hydrophilized metallic soap powder treated with polyoxyethylene (15) isostearyl ether (that is, the powder of Comparative Example 6) is prepared into a water-based eye shadow, the sense of use, cosmetic effect, and cosmetic durability are poorer than in the case where one treated with polyoxyethylene (10) isostearyl ether is used (that is, Example 19).

[Evaluation of Sense of Use, Cosmetic Effect, and Cosmetic Durability of Water-Based Makeup Base]

Water-based makeup bases having a composition shown in either of the following Example 20 and Comparative Example 21 were prepared, and the sense of use, cosmetic effect, and cosmetic durability of each water-based makeup base were evaluated.

(Preparation Method for Water-Based Makeup Base)

A: The powder components were well mixed.

B: BG of the aqueous layer component and the above component A were mixed and treated with a roller.

C: After A was added to B, the resultant was well stirred, whereby a water-based makeup base was obtained.
(Evaluation Methods for Sense of Use, Cosmetic Effect, and Cosmetic Durability)

The sense of use, cosmetic effect, and cosmetic durability of the water-based makeup base were evaluated in the same manner as the above-mentioned powder foundation.

TABLE 12

| | Components | Example 20 | Comparative Example 21 |
|---|---|---|---|
| Powder components | Hydrophobic silicone-treated talc | 7.0 (wt %) | 7.0 (wt %) |
| | Hydrophobic silicone-treated yellow iron oxide | 0.7 | 0.7 |
| | Hydrophobic silicone-treated red iron oxide | 0.3 | 0.3 |
| | Powder of Example 2 | 3.0 | — |
| | Powder of Comparative Example 3 | — | 3.0 |
| | Powder of Example 4 | 3.0 | — |
| | Powder of Comparative Example 5 | — | 3.0 |
| Aqueous layer components | BG | 10.0 | 10.0 |
| | Glycerin | 5.0 | 5.0 |
| | Ethanol | 9.0 | 9.0 |
| | EDTA·2Na | 0.2 | 0.2 |
| | Phenoxyethanol | 0.3 | 0.3 |
| | Ion exchanged water | balance | balance |
| Evaluation results | Sense of use | 4.6 | 3.5 |
| | Cosmetic effect | 4.5 | 3.6 |
| | Cosmetic durability | 4.2 | 3.5 |

From the evaluation results of Example 20, it was found that even if the hydrophilized amino acid powder treated with polyoxyethylene (10) isostearyl ether (that is, the powder of Example 2) and the hydrophilized polyurethane powder treated with polyoxyethylene (10) isostearyl ether (that is, the powder of Example 4) are prepared into a water-based makeup base, good sense of use, cosmetic effect, and cosmetic durability are obtained.

On the other hand, from the evaluation results of Comparative Example 21, it was found that when the hydrophilized amino acid powder treated with polyoxyethylene (15) isostearyl ether (that is, the powder of Comparative Example 3) and the hydrophilized polyurethane powder treated with polyoxyethylene (15) isostearyl ether (that is, the powder of Comparative Example 5) are prepared into a water-based makeup base, the sense of use, cosmetic effect, and cosmetic durability are poorer than in the case where one treated with polyoxyethylene (10) isostearyl ether is used (that is, Example 20).

[Evaluation of Sense of Use, Cosmetic Effect, and Cosmetic Durability of Antiperspirant]

Antiperspirants having a composition shown in either of the following Example 21 and Comparative Example 22 were prepared, and the stickiness, oily sensation, and comfort of each antiperspirant were evaluated.
(Preparation Method for Antiperspirant)
A: The powder components were well mixed.
B: The aqueous layer components were mixed and dissolved.
C: After A was added to B, the resultant was well stirred, whereby an antiperspirant was obtained.
(Evaluation Methods for Stickiness, Oily sensation, and Comfort)

The stickiness, oily sensation, and comfort of the antiperspirant were evaluated in the same manner as the above-mentioned water-based suncut lotion.

TABLE 13

| | Components | Example 21 | Comparative Example 22 |
|---|---|---|---|
| Powder components | Zinc oxide | 2.0 (wt %) | 2.0 (wt %) |
| | Powder of Example 3 | 3.5 | — |
| | Powder of Comparative Example 4 | — | 3.5 |
| | Powder of Example 4 | 6.0 | — |
| | Powder of Comparative Example 5 | — | 6.0 |
| Aqueous layer components | Sodium chloride | 0.1 | 0.1 |
| | Ethanol | 42.0 | 42.0 |
| | BG | 2.0 | 2.0 |
| | Polyoxyethylene sorbitan monolaurate | 0.2 | 0.2 |
| | Phenoxyethanol | 0.3 | 0.3 |
| | Ion exchanged water | balance | balance |
| Evaluation results | No stickiness | 4.5 | 3.7 |
| | No oily sensation | 4.7 | 3.3 |
| | Comfort | 4.5 | 3.5 |

From the evaluation results of Example 21, it was found that even if the hydrophilized silicone powder treated with polyoxyethylene (10) isostearyl ether (that is, the powder of Example 3) and the hydrophilized polyurethane powder treated with polyoxyethylene (10) isostearyl ether (that is, the powder of Example 4) are prepared into an antiperspirant, the antiperspirant is not sticky with no oily sensation, and good comfort is obtained.

On the other hand, from the evaluation results of Comparative Example 22, it was found that when the hydrophilized silicone powder treated with polyoxyethylene (15) isostearyl ether (that is, the powder of Comparative Example 4) and the hydrophilized polyurethane powder treated with polyoxyethylene (15) isostearyl ether (that is, the powder of Comparative Example 5) are prepared into an antiperspirant, the stickiness, oily sensation, and comfort are poorer than in the case where one treated with polyoxyethylene (10) isostearyl ether is used (that is, Example 21).

[Evaluation of Sense of Use, Cosmetic Effect, and Cosmetic Durability of Hair Treatment]

Hair treatments having a composition shown in either of the following Example 22 and Comparative Example 23 were prepared, and the stickiness, hair combability, and hair smoothness of each hair treatment were evaluated.
(Preparation Method for Hair Treatment)
A: The oil layer components were heated and mixed.
B: The aqueous layer components were dispersed and mixed.
C: After B was added to A, the resultant was well mixed, whereby a hair treatment was obtained.
(Evaluation Methods for Stickiness, Hair Combability, and Hair Smoothness)

The stickiness, hair combability, and hair smoothness of the hair treatment were evaluated based on the score on a five-point scale given by 25 expert panelists in the same manner as the above-mentioned powder foundation.

TABLE 14

| | Components | Example 22 | Comparative Example 23 |
|---|---|---|---|
| Oil layer components | Ethylene glycol distearate | 1.5 (wt %) | 1.5 (wt %) |
| | Liquid paraffin | 10.0 | 10.0 |
| | Squalene | 5.0 | 5.0 |
| | Stearyl alcohol | 1.5 | 1.5 |
| | Dimethylpolysiloxane (10 cs) | 3.5 | 3.5 |
| | Stearic acid | 5.0 | 5.0 |

TABLE 14-continued

| | Components | Example 22 | Comparative Example 23 |
|---|---|---|---|
| Aqueous layer components | Powder of Example 6 | 5.0 | — |
| | Powder of Comparative Example 7 | — | 5.0 |
| | Polyoxyethylene (3) stearyl alcohol | 4.5 | 4.5 |
| | Polyoxyethylene (10) cetyl ether | 2.0 | 2.0 |
| | BG | 6.0 | 6.0 |
| | Preservative | q.s. | q.s. |
| | Purified water | balance | balance |
| Evaluation results | No stickiness upon use | 4.3 | 3.8 |
| | Hair combability | 4.3 | 3.7 |
| | Hair smoothness | 4.5 | 3.6 |

From the evaluation results of Example 22, it was found that even if the hydrophilized silicone powder treated with polyoxyethylene (10) isostearyl ether (that is, the powder of Example 6) is prepared into a hair treatment, the hair treatment is not sticky upon use, and good hair combability and good hair smoothness are obtained.

On the other hand, from the evaluation results of Comparative Example 23, it was found that when the hydrophilized silicone powder prepared based on a known technology (that is, the powder of Comparative Example 7) is prepared into a hair treatment, the stickiness upon use, hair combability, and hair smoothness are poorer than in the case where one treated with polyoxyethylene (10) isostearyl ether is used (that is, Example 22).

CONCLUSION

As described above, it was found that the hydrophilized organic powder of the present invention having a hydrophilizing-coat of polyoxyethylene (10) isostearyl ether on a hydrophobic organic powder can achieve more favorable properties than a hydrophilized organic powder as a comparison target having a hydrophilizing-coat obtained by a hydrophilization treatment with polyoxyethylene (5) isostearyl ether or polyoxyethylene (15) isostearyl ether. That is, it was found that when a hydrophobic organic powder is subjected to a hydrophilization treatment with polyoxyethylene isostearyl ether, the degree of polymerization of polyoxyethylene is preferably 10 as compared with 5 or 15 in terms of hydrophilicity, ductility and adhesion, stability over time, sense of use, cosmetic effect, cosmetic durability, and the like.

What is claimed is:

1. A hydrophilized organic powder, comprising a hydrophilizing-coat of polyoxyethylene (10) isostearyl ether on a hydrophobic organic powder.

2. The hydrophilized organic powder according to claim 1, wherein the hydrophobic organic powder is an organic resin powder or a metallic soap powder, or a combination thereof.

3. A cosmetic, comprising the hydrophilized organic powder according to claim 1.

4. A cosmetic, comprising the hydrophilized organic powder according to claim 2.

* * * * *